(12) United States Patent
Stevie et al.

(10) Patent No.: US 6,229,141 B1
(45) Date of Patent: May 8, 2001

(54) ANALYSIS OF ALKALI ELEMENTS IN INSULATORS USING SECONDARY ION MASS SPECTROMETRY

(75) Inventors: Frederick A. Stevie; Jennifer M. McKinley, both of Orlando, FL (US)

(73) Assignee: Lucent Technologies, Inc., Murray Hill, NJ (US)

(*) Notice: Subject to any disclaimer, the term of this patent is extended or adjusted under 35 U.S.C. 154(b) by 0 days.

(21) Appl. No.: 09/138,740

(22) Filed: Aug. 24, 1998

(51) Int. Cl.[7] .................................. G01N 23/225
(52) U.S. Cl. ............................ 250/282; 250/309
(58) Field of Search ........................ 250/282, 309

(56) References Cited

PUBLICATIONS

F.A. Stevie, R.G. Wilson, J.M. McKinley, & C.J. Hitzman, "Multiple Element Ion Implants For Metal Contamination Analysis In Semiconductor Technology", *Quantitative Analysis*, pp. 983–986.

K. Nakatsu, S. Hatakey Ama, & S. Saito, "Charge Compresation in High–Resistivity Insulator Analysis with Electron Bombardment by CAMECA IMS 4f", *Secondary Ion Mass Spectrometry SIMS XL*, Proceedings of the Eleventh International Conference on Secondary Ion Mass Spectrometry, Sep. 7–12th, 1997, John Wiley & Sons.

F.A. Stevie, "Secondary Ion Mass Spectrometry–First Microelectronics, Now the Rest of the World", *Surface And Interface Analysis*, vol. 18, pp. 81–86, (1992).

C.W. Magee & W.L. Harrington, "Depth Profiling of Sodium in $SiO_2$ Films by Secondary Ion Mass Spectrometry", *Appl. Phys. Lett.*, vol. 33(2), Jul. 15, 1978.

F.A. Stevie, V.V.S. Rana, A.S. Harrus, T.H. Briggs, P. Skeath, "Summary Abstract: High Sputter Rate Secondary Ion Mass Spectrometry Analysis of Insulators Used in Microelectronica and Lightwave Applications", *J. Vac. Sci. Technol. A*, vol. 6(3), May/Jun 1988, pp. 2082–2084.

Charles Evans & Associates, "The CEA Online Tutorial" including sections on SIMS Theory and SIMS Instrumentation, http://www.cea.com/tutorial.htm, Copyright 1995.

*Primary Examiner*—Jack Berman

(57) ABSTRACT

A method for utilizing secondary ion mass spectrometry (SIMS) analysis allows for the accurate determination of alkali elements in insulator materials by controlling the penetration depth of an electron beam used for charge neutralization so as to minimize the movement of alkali elements in the insulator. The method can be employed in connection with both magnetic sector SIMS instruments and quadrupole SIMS instruments.

37 Claims, 6 Drawing Sheets

ANALYSIS OF ALKALI ELEMENTS IN INSULATORS USING SECONDARY ION MASS SPECTROMETRY

FIELD OF THE INVENTION

This invention relates to an improved method for utilizing secondary ion mass spectrometry (SIMS) analysis in connection with insulator materials. More particularly, the invention involves an improved method for charge neutralization that can be used in connection with a SIMS analysis of insulators.

BACKGROUND OF THE INVENTION

Secondary ion mass spectrometry (SIMS) has become a purity analysis method of choice for surface and near surface investigation of solid samples because of its ability to provide parts-per-million to parts-per-billion sensitivity and excellent depth resolution. SIMS relates to a technique for surface and near surface analysis which involves ion bombardment of the sample surface for depth profiling. A good tutorial relating to the SIMS technique can be found on the Internet at http://www.cea.com/tutorial.htm, which is incorporated by reference in its entirety.

As discussed therein, SIMS involves the use of a bombarding primary ion beam onto a sample. Primary ions are implanted and mix with sample atoms to depths of 1 to 10 nm depending on the bombarding energy. The bombarding ion produces monatomic and polyatomic neutrals and ions of sample material, resputtered primary ions, as well as electrons and photons. Sputter rates depend on primary beam intensity, sample material, and crystal orientation. Sputter rates in typical SIMS analyses vary between 0.5 and 5 nm/s.

The primary ion beam species that are typically useful in SIMS analysis include $Cs^+$, $O^{2+}$, $O^-$, $Ar^+$, and $Ga^+$ at energies between 1 and 30 keV.

SIMS instruments include both static SIMS instruments, e.g., time-of-flight instruments, and dynamic SIMS instruments. Dynamic SIMS instruments in turn primarily employ use two kinds of mass analyzers, magnetic sector and quadrupole analyzers.

Magnetic sector instruments are common in the field. In these instruments, the ion beam passes through the magnetic field where the particles are acted on by a force at right angles, both to the direction of motion and to the direction of the magnetic field. Modern mass spectrometers use non-normal pole faces for entrance and exit of the ion beam to the magnetic sector. The fringings fields in this configuration compress the ion beam in the vertical direction (in and out of the screen) as it passes through the sector. Fewer ions strike metal surfaces and the ion beam focuses better at the exit slit with non-normal pole faces. The entrance and exit slits can be arranged at ion beam crossovers for the cleanest separation (highest mass resolution) between ions with similar m/z values.

Quadrupole mass analyzers, on the other hand, have been employed in many kinds of analysis since their invention in 1953. Quadrupole analysis employ rods that ideally have hyperbolic shapes, but this geometry can be approximated with closely spaced circular rods. In a typical quadrupole spectrometer, the rods are 1 cm in diameter and 20 cm long. Ions enter at a relatively low energy (~25 eV). Alternating and direct voltages on the rods cause the ions to oscillate after entering the quadrupole. For a given set of voltages, ions with a single mass-to-charge ratio undergo stable oscillation and traverse through the rods. All other ions have unstable oscillations and strike the rods. The alternating frequency and the ratio between the alternating and direct voltages remain constant.

The widespread use of SIMS technology can be seen, for example, from the article "Secondary Ion Mass Spectrometry—First Microelectronics, Now the Rest of the World", by F. A. Stevie, *Surface and Interface Analysis*, Vol. 18, 81–86 (1992), which is incorporated by reference in its entirety.

The use of SIMS in connection with insulating materials is also known. However, it has also suffered from a number of problems. As shown in FIG. 1, ion bombardment 1, of an insulating surface 2, induces a positive charge 3, onto the oxide surface. This problem has been addressed by a variety of approaches, the most common of which involves the use of an electron beam 4, that seeks to neutralize the positive ion buildup. Electron beam neutralization has been used in connection with both magnetic sector and quadrupole based SIMS instruments.

Despite the effectiveness of electron beam neutralization in connection with quadrupole and magnetic sector instruments, there are nonetheless significant limitations on the use of SIMS in certain environments. One specific area in which SIMS analysis, and in particular magnetic sector based SIMS analysis, has not been effective involves the determination of alkali elements in insulators.

This problem is not unknown in the art and as was discussed, for example, in "Depth Profiling of Sodium in $SiO_2$ Films by Secondary Ion Spectrometry", C. W. Magee et al., *Applied Physics Letters*, 33, 193 (1978).

Traditional SIMS analysis of alkali metals in insulators has been deficient because the alkali elements will, in essence, "move" when an electric field is applied during SIMS testing. Such movement provides a false negative, i.e., will appear to indicate that the alkali metals are not present when in fact they are present in the insulator or, alternatively, will not show the proper location of the alkali elements.

The ability to accurately determine the presence of alkali elements as well as their quantity and exact location in insulators is particularly critical in the manufacture of semiconductor materials. The movement of alkali elements in the insulator under application of an electric field results in an insulator that acts as a conductor. Thus, insulators including alkali elements are largely useless in the field of electronic devices.

The primary technique that the art has employed in order to minimize this problem has involved the introduction of a conductive film coating onto the surface of the insulator. However, such a coating can introduce significant contamination problems during fabrication. Thus, it is an unacceptable solution to the problem of alkali metal movement in the field of semiconductor manufacture.

Accordingly, the need still exists for a method for accurately analyzing alkali elements in insulators.

SUMMARY OF THE INVENTION

Among other aspects, the present invention is based upon the surprising discovery that controlling the depth of electron penetration during charge neutralization in SIMS is effective in solving the problem of alkali element mobility and providing an accurate determination regarding the presence of alkali elements in an insulator.

Accordingly, the invention involves an improved secondary ion mass spectrometry (SIMS) analysis of an insulator that employs the use of an electron beam in charge neutralization. In particular, the method provides for controlling the electron penetration depth so as to at least substantially minimize the movement of alkali elements in the insulator.

In one aspect of the invention, the present invention relates to a method for charge neutralization in SIMS analysis using magnetic sector analysis. This method involves:

(a) providing a material having an insulator layer thereon;

(b) applying an ion beam onto a region of the surface of the insulator; and (c) applying an electron beam onto at least a portion of the ion beam region, wherein the depth of electron penetration is not substantially greater than the depth of the dielectric layer.

This method can be used where the insulators is present on a substrate or where the insulator is present on another layer which itself is directly or indirectly on a substrate.

In another aspect, the claimed invention relates to a method for charge neutralization in SIMS analysis using a quadrupole instrument. This method comprises:

(a) providing an insulator material;

(b) applying an ion beam onto a region of the surface of the insulator material; and (c) applying an electron beam onto at least a portion of the region such that the depth of electron penetration is not substantially greater than the depth of ion penetration.

The inventive method can be used in a variety of environments including, for example, the testing of wafer(s) employed in the manufacture of integrated circuits.

DETAILED DESCRIPTION OF THE PREFERRED EMBODIMENT OF THE INVENTION

Figure 1:
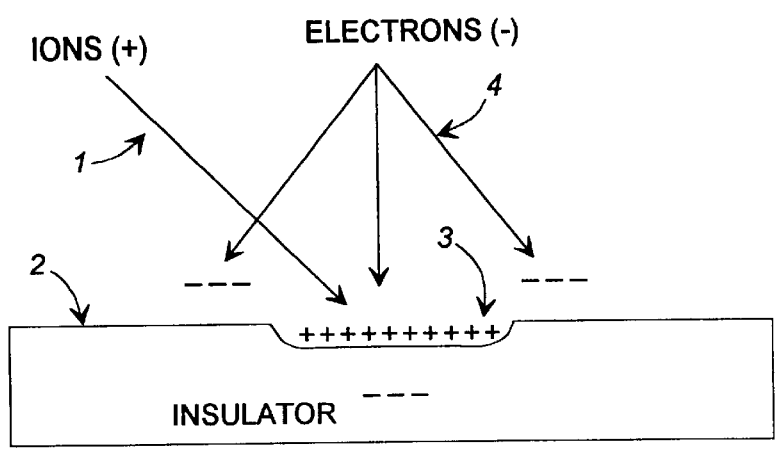
FIG. 1 schematically illustrates the undesirable positive ion buildup during SIMS analysis of insulators in the absence of neutralization.

The invention relates to an improved method for charge neutralization during SIMS analysis of an insulator. This aspect of the invention involves controlling the depth of electron penetration during charge neutralization so as to substantially minimize, or even completely eliminate, movement of the alkali elements during the analysis.

By "at least substantially minimizing" it is meant that although there may be some alkali element mobility in the insulator, the resulting SIMS profile is nonetheless sufficient to calibrate for subsequent measurements on a sample with an unknown alkali content.

First of all, the inventive method can be used in connection with any primary ion beam species recognized in the art as being useful in SIMS analysis including but not limited to $Cs^+$, $O^{2+}$, $O^-$, $Ar^+$, and $Ga^+$ at energies between 1 and 30 keV.

Moreover, the electron beam charge neutralization technique of the invention can be effectively employed in connection with dynamic SIMS techniques, including both magnetic sector and quadrupole SIMS instruments. However, the precise optimization differs from one type of instrument to another.

In order to appreciate the differences, it is important to recognize certain differences between the quadrupole and magnetic sector instruments. Attention in this regard is directed toward FIGS. 2 and 3 that schematically illustrate magnetic sector and quadrupole instruments, respectively.

Quantitatively, quadrupole results are typically easier to obtain because the extraction voltages are on the order of a few hundred volts. This is in direct contrast to the magnetic sector instrument in which the extraction voltages are on the order of thousands of volts. Moreover, the quadrupole device has a more "open" geometry of the sample area that permits the electron gun to be more optimally positioned. Despite these differences, both instruments can be readily employed in the context of this invention. In each case, the inventive method involves controlling the electron penetration depth so as to substantially minimize or eliminate alkali element movement.

Although the precise "optimized depth" differs between magnetic sector and quadrupole instruments, in both cases, it is first necessary to determine electron penetration depth in the insulator. To this end, it is known that electron penetration depth can be determined by the way of the Kanaya-Okayama equation:

$$R = [(0.0276A)/Z^{0.89}\rho]E_0^{1.67}$$

where Z=atomic number
A=atomic weight (g/mole)
$\rho$=density (g/cm$^3$)
$E_0$=beam energy (keV)
R=maximum depth of electron penetration ($\mu$m)

As can be seen, the depth of penetration is directly related to the energy of the electron beam. Thus, for any desired electron beam, those skilled in the art can determine the maximum depth.

In turning first to magnetic sector based SIMS instrument, the optimum penetration of electron depth corresponds to the thickness of the insulator layer. That is, as illustrated schematically by FIG. 2, the depth of the electron penetration, 11, substantially corresponds to the thickness of the insulator on the substrate.

By "substantially corresponds" it is meant that the depth of penetration is not substantially greater than that which substantively minimizes or eliminates alkali element movement in the insulator. Depending upon the particular insulator being analyzed, this is typically a depth that is less than 50% greater than the thickness of the insulator, with a depth of less than 10% greater than the thickness of the insulator layer being more preferred and a depth less than 5% greater being even more preferred. Insofar as the key parameter related to the thickness of the insulator, those skilled in the art would be readily capable of optimizing the depth of penetration for an electron beam for a particular insulator.

Figure 2:
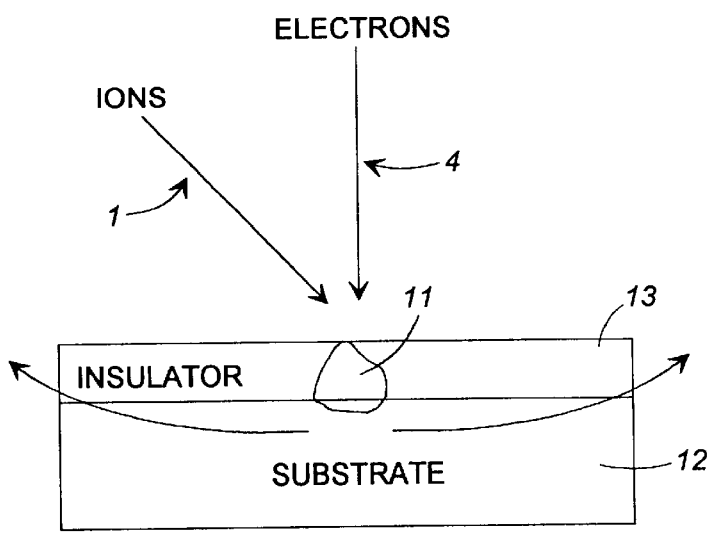
FIGS. 2 and 3, provide schematic illustration of neutralization methods according to the invention.

Because the electron beam depth is related to the thickness of the insulator material, the inventive method preferably employed an arrangement such as that of FIG. 2, where a substrate, 12, is coated with a dielectric layer, 13.

Although a two-layer arrangement is illustrated, the invention is not limited to such arrangements. For example, while the insulator can be on a substrate, the insulator can be present on another layer that is itself directly or indirectly located on a substrate. In any case, it is preferred that the insulator layer be present on a conductive material.

In yet another embodiment, the method can also be used in connection with composite materials where a coating layer, e.g., a conductive coating layer is present on the dielectric.

The inventive method can be used with any of the insulator materials recognized in the art including, but not limited to, $SiO_2$, $Si_3N_4$, borosilicate glass (BSG), phosphosilicate glass (PSG) and borophosphosilicate glass (BPSG). Other examples of insulators include paints, plastics, seashells or even rock.

Moreover, the nature of the material onto which is insulator is introduced is dependent only on the environment in which the device is to be ultimately used. That is, the inventive method can be used in connection with any substrate or layer suitable for use with an insulator material. For example, where introduced onto a substrate, typical substrates in the semiconductor arena would be silicon or germanium silicon.

On the other hand, where the insulator is introduced onto a layer that is directly or indirectly located on a substrate, the layer is preferably a conductive material such as aluminum, copper, tungsten or titanium nitride, among others.

Finally, examples of suitable magnetic sector instruments include those produced by CAMECA Instruments, Courbevoie, France, such as the CAMECA IMS-3F, IMS4F, IMS-5F, and IMS-6F.

The inventive method can also be used in connection with quadrupole instruments. Examples of suitable quadrupole instruments include those produced by Physical Electronics. As discussed above, the quadrupole instrument differs from the magnetic sector instrument particularly in terms of the voltage of the secondary ions employed.

Figure 3:
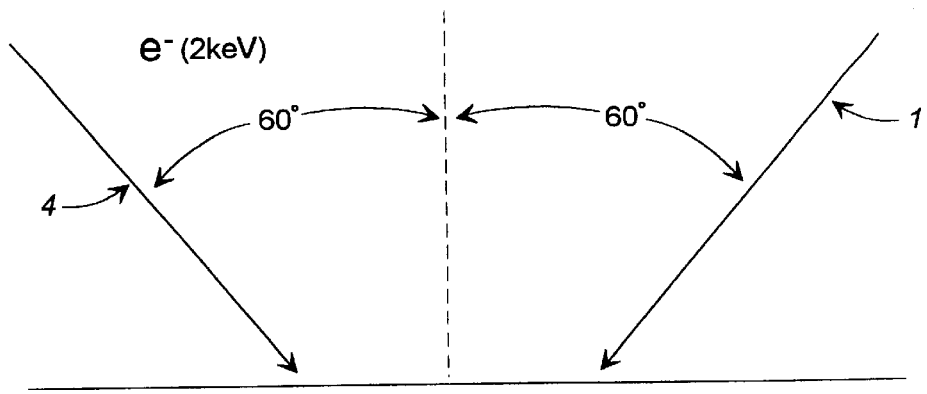

As illustrated in FIG. 3, the optimal control of the penetration of the electron beam involves matching the depth of penetration of the electron beam, 4, to the depth of penetration of the ion beam, 1. Moreover, it is preferred that this match be maintained as material is sputtered away by the ion beam/electron beam combination.

By "matching" in this regard, it is preferred that the penetration of the electron is not more than 50% greater than the depth of the penetration of the ion beam. Preferably, the electron beam does not penetrate more than 10% further into the dielectric than the ion beam with not greater than 5% being even more preferred. Once again, because the key parameter involves matching the electron beam to the ion beam, those skilled in the art would be able to optimize the electron beam for any particular ion beam/insulator combination.

Furthermore, since optimization is related to the ion beam rather than the thickness of the dielectric, this technique can be used in connection with bulk insulators in addition to the insulator film/substrate combination discussed above. FIG. 3 provides a schematic illustration of the inventive method in connection with a typical quadrupole instrument.

Once again, the type of insulator employed does not limit the method; instead, it can be employed with any insulator materials recognized in the art. Examples of insulators include $LiNbO_3$ and $Al_2O_3$. On the other hand, examples of insulators on substrates include silicon oxide/silicon and silicon oxide/aluminum.

The inventive method is capable of minimizing, and even eliminating, the movement of alkali elements in the dielectric. Accordingly, the method allows for the viable use of both magnetic sector and quadrupole instruments for the SIMS analysis of insulators.

The inventive method can be used in a variety of environments. For example, it can be employed as an analytic technique in connection with the manufacture of integrated circuits. To this end, the method can be used during wafer fabrication to test, e.g., one or more wafers from a lot of wafers. This technique will allow for the accurate determination of alkali element concentration and thus whether the wafers can be effectively employed in making integrated circuits.

The present invention will now be illustrated by the following examples. However, it should be recognized that these examples are only illustrative in nature and in no way limit the scope of the inventive method.

EXAMPLES 1 & 2

Figure 4:
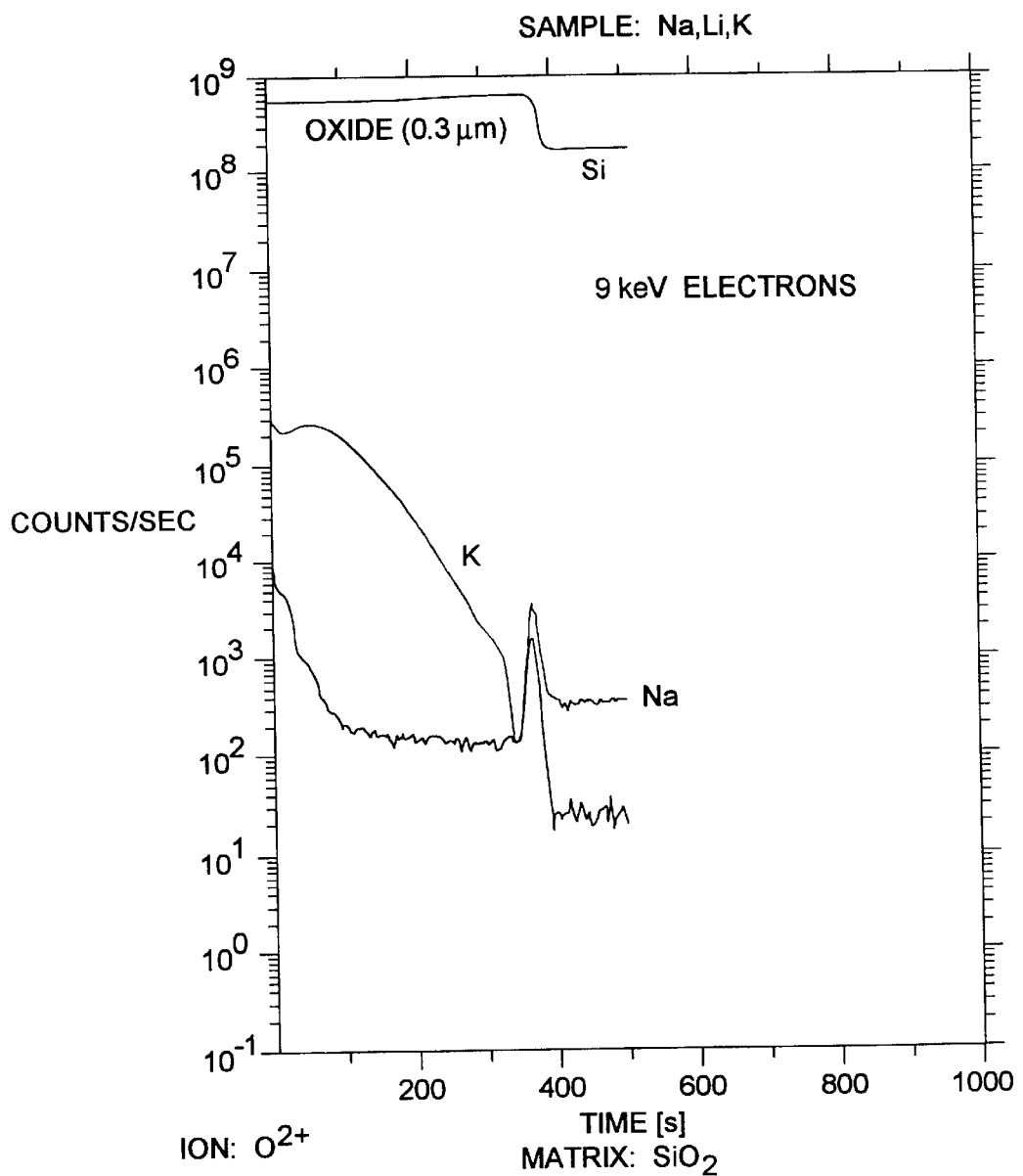
FIGS. 4–8 illustrate the results of both examples of SIMS analysis according to the invention and comparative examples.

These comparative examples illustrate the difficulty of determining the presence of alkali elements such as sodium in insulating materials. In this example, an electron beam of 9 keV having a depth penetration of 1.3 $\mu$m was introduced onto a sample having an oxide layer of 0.3 $\mu$m on a silicon substrate. The oxide layer includes Na, Li and K ions that have been implanted. As illustrated by FIG. 4, the sodium ions moved within the sample during testing.

Figure 5:
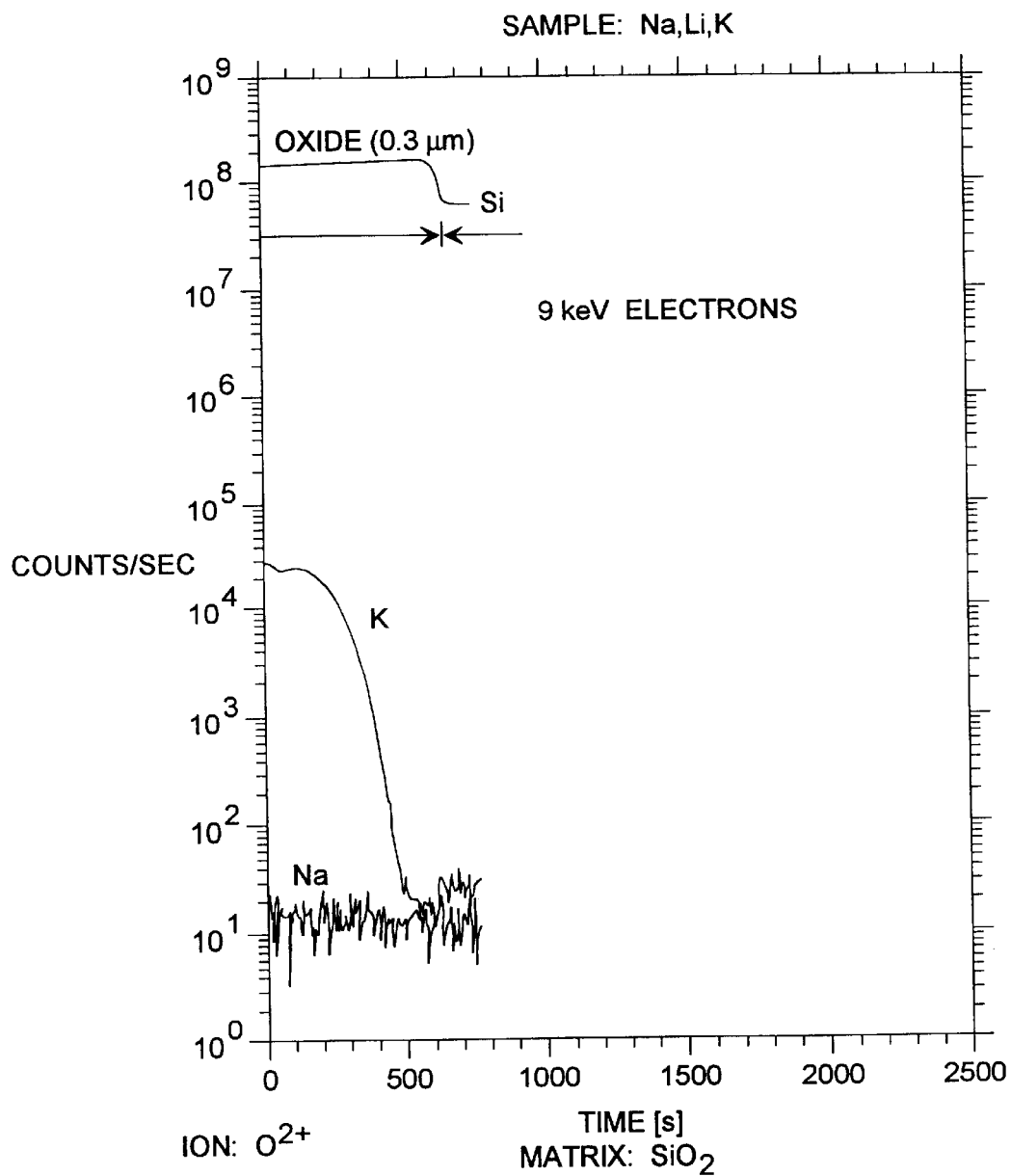

Example 2 repeats Example 1 with the results illustrated by FIG. 5 showing a false negative regarding the presence of sodium ion.

EXAMPLE 3

Figure 6:
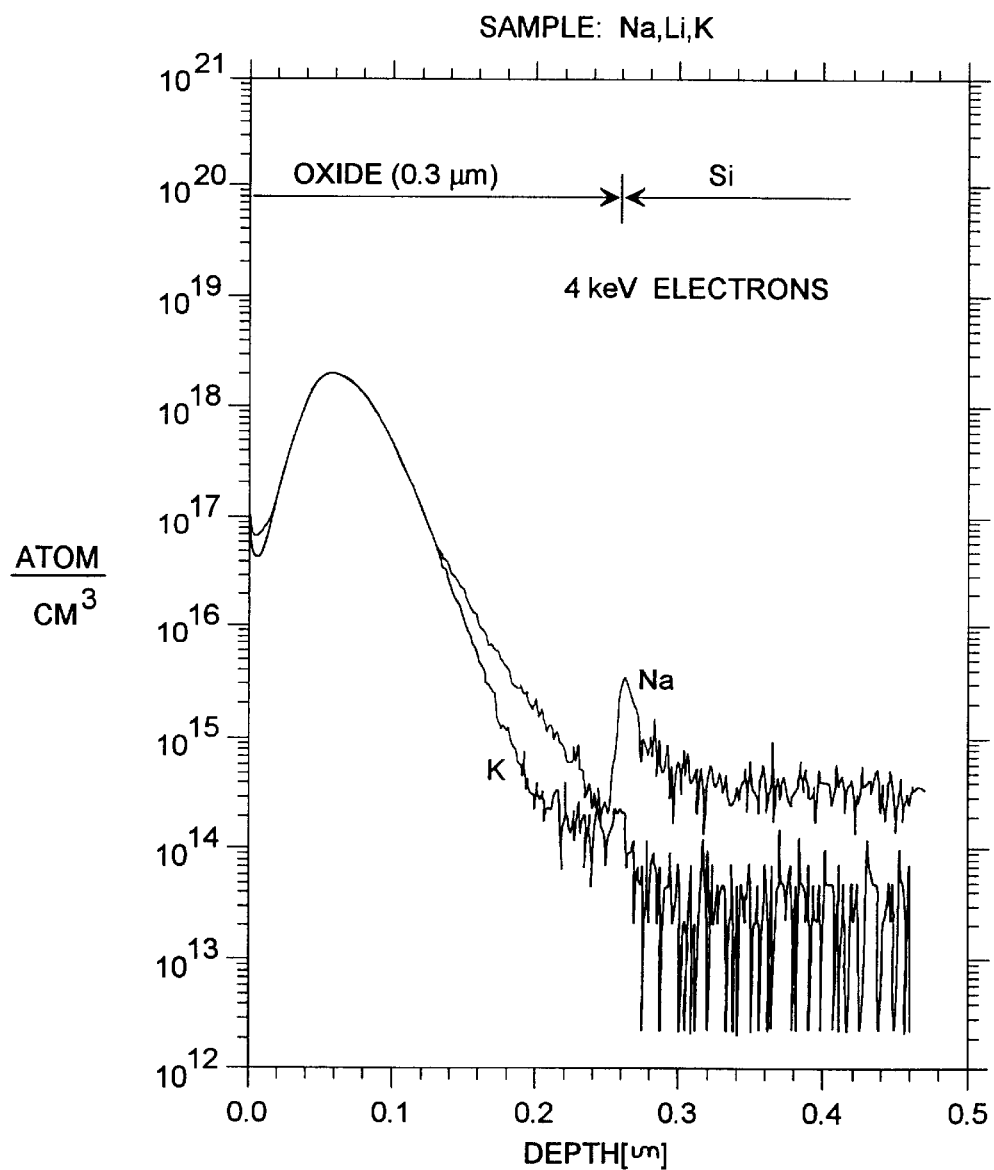

This example also illustrates the use of the magnetic sector instrument on a sample having a 0.3 $\mu$m oxide layer on silicon. Once again, Na, Li and K were present in the sample. An electron beam of 4 keV having a depth of penetration of 0.3 $\mu$m is employed. The results illustrated by the graph of FIG. 6 confirm the presence of the elements in the insulator.

EXAMPLE 4

Figure 7:
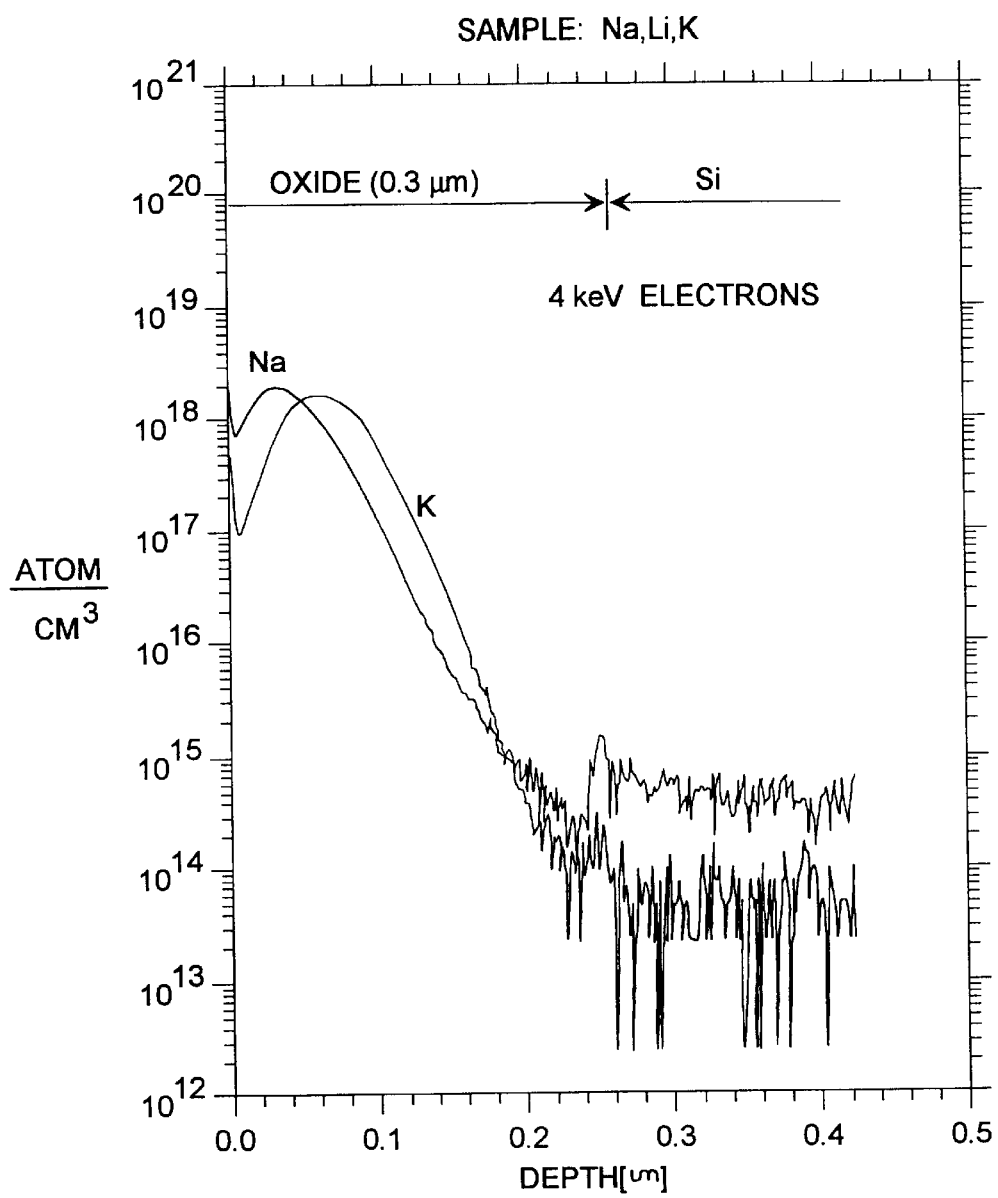

The method of Example 3 was repeated in an adjacent region and the results are shown by the graph of FIG. 7. This example confirms the repeatability of the inventive method in determining the presence and amount of alkali elements in the insulator.

EXAMPLE 5

Figure 8:
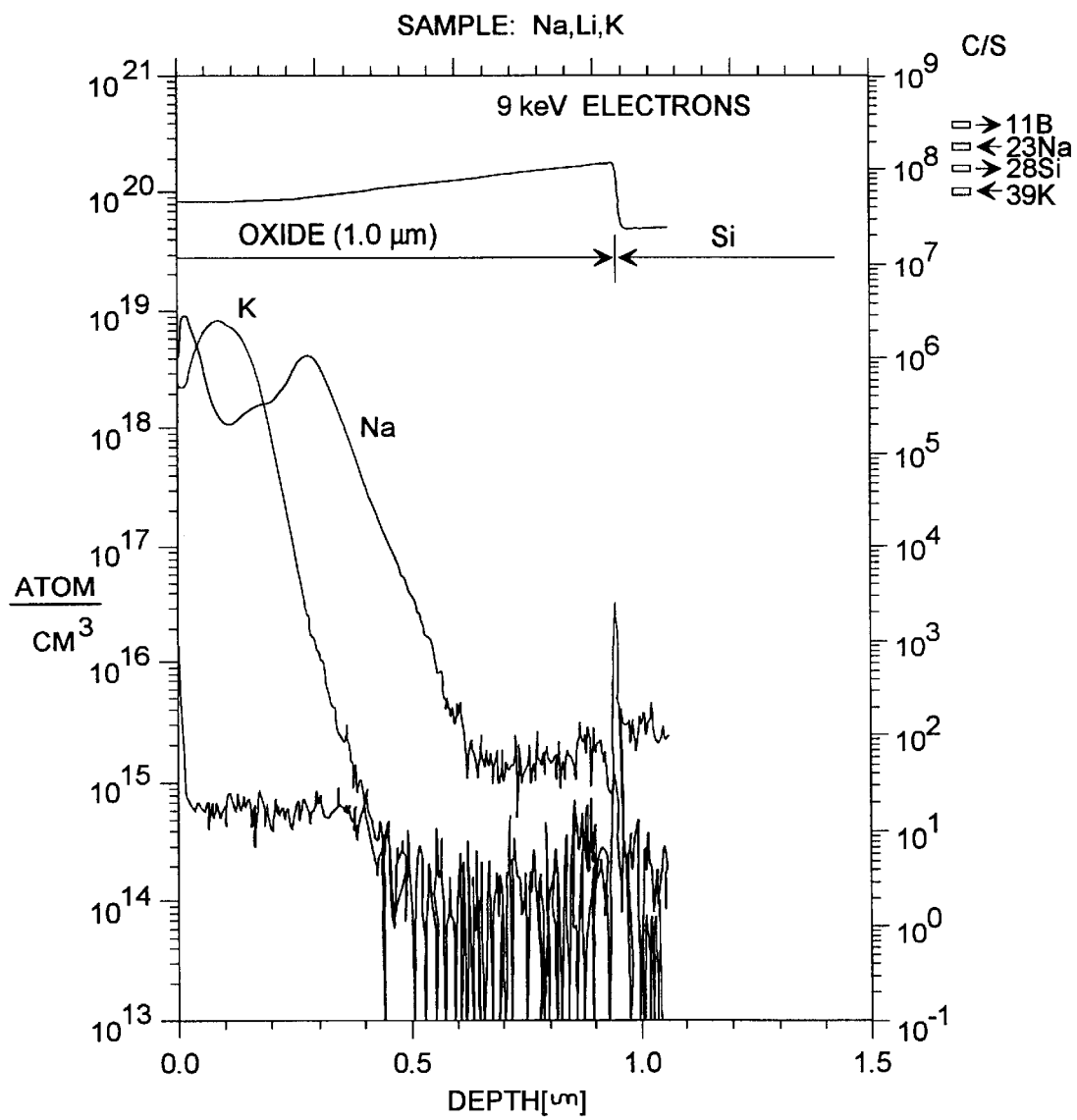

This example having a 1.0 $\mu$m oxide layer on a silicon substrate was employed. The electron beam used in charge neutralization was 9 keV having a depth penetration of 1.3 $\mu$m. The results, which are illustrated by the graph of FIG. 8, once again confirm the ability to determine the level of alkali elements in the insulator layer.

While the present invention has been described in terms of various preferred embodiments thereof, it will be illustrated that various modifications, substitutions, omissions, and changes may be made without departing from the spirit thereof Accordingly, it is intended that the scope of the present invention be limited only by the scope of the following claims including equivalents thereof.

What is claimed is:

1. A method for charge neutralization in SIMS analysis using a magnetic sector instrument comprising:
    (a) providing a material having an insulator layer thereon;
    (b) applying an ion beam onto a region of the surface of the insulator; and
    (c) applying an electron beam onto at least a portion of the ion beam region wherein the depth of electron penetration is a distance greater than 100% and less than about 150% of the thickness of the insulator layer.

2. The method according to claim 1 wherein the material of step (a) is a conductive material.

3. The material according to claim 1 wherein the material of step (a) is a substrate.

4. The material according to claim 1 wherein the material of step (a) is a layer that is either directly or indirectly located on a substrate.

5. The material according to claim 1 wherein the depth of electron penetration is a distance equal to about 110% of the thickness of the insulator.

6. The material according to claim 1 wherein the depth of electron penetration is a distance equal to about 105% of the thickness of the insulator.

7. The method according to claim 1 wherein the insulator thickness is from 0.1–2 µm.

8. The method according to claim 7 wherein the insulator thickness is from 0.5–1.5 µm.

9. The method according to claim 3 wherein the substrate comprises silicon or germanium silicon.

10. The method according to claim 4 wherein the layer comprises aluminum, copper, tungsten, or titanium nitride.

11. The method according to claim 1 wherein the insulator layer comprises a silicon oxide, silicon nitride, borosilicate glass (BSG), phosphosilicate glass (PSG) and borophosphosilicate glass (BPSG).

12. The method according to claim 1 further comprising a coating layer on the surface of the insulator layer and the depth of electron penetration is a distance equal to from about 105 to about 150% greater than the combined thickness of the coating layer and the insulator layer.

13. The method according to claim 12 wherein the coating comprises a conductive material.

14. A method for charged neutralization in SIMS analysis using a quadrapole instrument comprising:
    (a) providing an insulator material
    (b) applying an electron beam onto at least a portion of the insulator material;
    (c) applying an electron beam onto at least a portion of the region such that the depth of electron penetration is a distance equal to from about 105% to about 150% of the depth of penetration of the ion beam.

15. The method according to claim 14 wherein the depth of electron penetration is a distance equal to from about 5% to 50% greater than the depth of ion penetration.

16. The method according to claim 14 wherein the depth of electron penetration is a distance equal to from about 5% to 10% greater than the depth of ion penetration.

17. The method according to claim 14 wherein the insulator material is a layer that is either directly or indirectly on a substrate.

18. The method according to claim 17 wherein the substrate comprises silicon or germanium silicon.

19. The method according to claim 17 wherein the insulator material comprises silicon oxide, silicon nitride, borosilicate glass (BSG), phosphosilicate glass (PSG) and borophosphosilicate glass (BPSG).

20. A method for charge neutralization of an insulator surface using SIMS analysis comprising controlling the electron penetration depth such that the penetration depth of the electron beam is a distance greater than 100% and less than about 150% of the penetration depth of the ion beam.

21. The method according to claim 20, wherein the electron penetration depth is about 10% greater than the ion penetration depth.

22. The method according to claim 20, wherein the electron penetration depth is about 5% greater than the ion penetration depth.

23. A method for testing wafers used in manufacturing integrated circuits comprising:
    (a) providing a wafer including an insulator layer;
    (b) applying an ion beam onto a region of the surface of the insulator; and
    (c) applying an electron beam onto the surface of the insulator for charge neutralization such that the electron penetration depth is a distance greater than 100% and less than about 150% of the depth of an ion beam penetration depth to at least substantially minimize the movement of alkali elements in the insulator.

24. The method according to claim 23, wherein the electron penetration depth is a distance equal to about 110% of the ion beam penetration depth.

25. The method according to claim 23, wherein the electron penetration depth is a distance equal to about 105% of the ion beam penetration depth.

26. A method for making integrated circuits including wafer fabrication comprising:
    (a) providing a material having an insulator layer thereon;
    (b) applying an ion beam onto a region of the surface of the insulator; and
    (c) applying an electron beam onto at least a portion of the ion beam region wherein the depth of electron penetration is a distance greater than 100% and less than about 150% of the thickness of the insulator layer.

27. The method according to claim 26, wherein the electron penetration depth is a distance equal to about 110% of the insulator thickness.

28. The method according to claim 26, wherein the electron penetration depth is than a distance equal to about 105% of the insulator thickness.

29. A method for making integrated circuits including wafer fabrication comprising:
    (a) providing a material having an insulator layer thereon;
    (b) applying an ion beam onto a region of the surface of the insulator; and
    (c) applying an electron beam onto at least a portion of the ion beam region wherein the depth of electron penetration is a distance greater than 100% and less than about 150% of the penetration of the ion beam.

30. The method according to claim 29, wherein the electron penetration depth is a distance equal to about 110% of the ion penetration depth.

31. The method according to claim 29, wherein the electron penetration depth is than a distance equal to about 105% of the ion penetration depth.

32. A method for charge neutralization of an insulator surface using SIMS analysis comprising controlling the electron penetration depth, such that said electron penetration depth is a distance greater than 100% and less than about 150% of the insulator thickness.

33. The method according to claim 32, wherein the electron penetration depth is a distance equal to about 110% of the insulator thickness.

34. The method according to claim 32, wherein the electron penetration depth is a distance equal to about 105% of the insulator thickness.

35. A method for testing wafers used in manufacturing integrated circuits comprising:
    (a) providing a wafer including an insulator layer;
    (b) applying an ion beam onto a region of the surface of the insulator; and
    (c) applying an electron beam onto the surface of the insulator for charge neutralization such that the electron penetration depth is a distance greater than 100% and less than about 150% of the insulator thickness to at least substantially minimize the movement of alkali elements in the insulator.

36. The method according to claim 35, wherein the electron penetration depth is about 110% of the insulator thickness.

37. The method according to claim 35, wherein the electron penetration depth is about 105% of the insulator thickness.

* * * * *